United States Patent [19]
Berthoux et al.

[11] 3,959,347
[45] May 25, 1976

[54] MANUFACTURE OF ALKYL ESTERS OF POLYCARBOXYLIC ACIDS

[75] Inventors: Jean Berthoux, Decines; Ghislain Schwachhofer, Miribel, both of France

[73] Assignee: Rhone-Progil, Paris, France

[22] Filed: June 25, 1973

[21] Appl. No.: 372,956

[30] Foreign Application Priority Data
July 31, 1972 France ............................ 72.28141

[52] U.S. Cl. ...................... 260/468 K; 260/475 R; 260/485 R
[51] Int. Cl.² ........................................ C07C 67/10
[58] Field of Search ......... 260/475 R, 468 K, 485 R

[56] References Cited
UNITED STATES PATENTS
3,574,706  4/1971  Cevidalli et al. .................... 260/475

FOREIGN PATENTS OR APPLICATIONS
917,568    2/1963  United Kingdom ................. 260/475
916,772    1/1963  United Kingdom ................. 260/475
2,245,457  3/1973  Germany ............................ 260/475

*Primary Examiner*—Lorraine A. Weinberger
*Assistant Examiner*—Jane S. Myers
*Attorney, Agent, or Firm*—Browdy and Neimark

[57] ABSTRACT

A method of making alkyl esters of polycarboxylic acids by reacting an alkaline salt of the acid and at least one halo-alkane so that the rate of conversion is limited to 35–85% whereby no partial esters are formed.

6 Claims, No Drawings

MANUFACTURE OF ALKYL ESTERS OF POLYCARBOXYLIC ACIDS

FIELD OF INVENTION

The present invention relates to improvements in a process for the manufacture of alkyl esters of polycarboxylic acids by the reaction of alkaline salts of the acids with halo-alkanes. In the present description, the term "alkyl esters" (or simply "esters") means the neutral esters of polycarboxylic acids, that is to say, the esters in which all the acid groups are substituted by the alkyl residues.

BACKGROUND OF THE INVENTION

In the prior U.S. patent application Ser. No. 287,412 filed on Sept. 8, 1972, a process for the manufacture of alkyl esters of carboxylic acids is described, which consists in reacting a halo-alkane with an alkaline salt of the acid in an heterogeneous organic-aqueous medium, in the presence of a catalytic quantity of a compound chosen from ammonia, primary, secondary and tertiary amines, and the salts of quaternary ammonium, containing altogether at least 10 carbon atoms in the molecule. In these applications, it is recommended to carry on the reaction for a period of time sufficient for the quasi-total reaction of the acid. When the starting acid is polycarboxylic, there is obtained, besides the desired product, intermediate acid esters (named hereinafter partial esters), that is to say, compounds in which the acid residues are not completely esterified. So as to separate these compounds from the reaction mixture, a washing of the organic phase is conducted with an alkaline solution which extracts the acid products, after removal of an aqueous phase containing the alkaline halide. This solution is recycled just as it is to the initial reaction.

When carrying on work in this field, it has been noted that this operating method has drawbacks to the process, for the washing solution is difficult and slow to separate by decantation. Moreover it has been noted that the partial esters recycled to the reaction undergo an hydrolysis.

SUMMARY OF THE INVENTION

There has now been found a means for remedying these drawbacks by means of a modification of the basic process, which results in the suppression of the formation of acid esters, and which leads to obtain purer alkyl esters. Further improvement will be apparent in the following description.

The invention depends on the surprising discovery according to which, contrary to what was expected, the contact of the carboxylic reactant with the halo-alkane leads first, to the formation of the neutral ester then, at the end of the reaction, to the formation of acid esters. The process of the present invention is particularly adapted to the reaction techniques described in the aforesaid patent application and will be explained in more detail hereinafter in connection with these methods. However, it can also be utilized in association with any other known processes of manufacture of esters of polycarboxylic acids, whenever the formation of acid esters is not desired.

DESCRIPTION OF PREFERRED EMBODIMENTS

According to the invention, esters can be prepared with alkyl linear or branched groups of the desired length, but contain particularly 6–20 carbon atoms, and carboxylic groups derived from saturated or unsaturated aliphatic, cyclo-aliphatic, aromatic, alkylaromatic di- or polyacids, such as succinic, maleic, adipic, ortho- iso- or terephthalic, or trimellitic acids.

The starting halo-alkanes can be pure or technical compounds. The 1-halo-alkanes are generally used, but the 2-halo-alkanes can equally be used as starting material. 1-bromo-alkanes are preferred on account of their ease of production but chloro-alkanes can also be employed. The alkaline salts of carboxylic acids can be pure or technical products and these compounds can be employed in a crystalline form, or can be manufactured in situ by contacting the alkaline hydroxide and the carboxylic acid, or its corresponding anhydride, in an aqueous medium, but in any case, it is advisable to avoid the presence of a noticeable excess of the hydroxide. It has been noted that if the hydroxide is found in the reaction mixture, in a quantity higher than about 3% in relation to the acid functions, the reaction of the salt with the halo-alkane is greatly reduced.

According to the main characteristic of the process according to the present invention, the conversion rate of the alkaline salt of the polycarboxylic acid, i.e. the esterification of the acid function, is limited. The conversion degree which must not be exceeded is not absolutely strict and can vary in certain limits, principally as a function of the polycarboxylic reaction used. In an indicative way, it can be said that generally the rate of conversion of the salt must be between about 35 and 85%. Practically, this purpose is achieved when starting from known processes, by acting on one or several factors which determines the rate of conversion of the salt and/or the rate of the reaction.

With the purpose of a better understanding of the object of the invention, methods of manufacture of alkyl esters of carboxylic acids are referred to hereafter, which are described in the patent application quoted above, and it is shown how these techniques can be modified so as to carry out the present process. The operative conditions indicated in the above-mentioned application are principally as follows:

- the relative proportions of halo-alkanes and of alkaline salts of carboxylic acids can be near the stoichiometry, but an excess of halo-alkane is preferred.
- the process is conducted in the presence of water, the proportion of which is advantageously between 50 and 200 g. per mole of halo-alkane.
- the catalyst is a nitrogen compound, chosen from the group containing ammonia, primary, secondary, and tertiary amines, and the quaternary ammonium salts containing at least 10 carbon atoms in their molecule. The more active compounds are the methylamine, ethylamine, dimethyl- and diethylamine, tetrabutylammonium bromide and morpholine. The quantity of catalyst introduced is in the order of about 0.5 to 5%, particularly about 1 to 3%, in molar percentage in relation with the alkaline salt of polycarboxylic acid.
- The temperature is generally kept between about 110° and 250°C., more particularly between 130° and 200°C.
- The reaction time is the more often between 30 minutes and 6 hours.
- The process is preferably conducted under the autogenous pressure, but higher pressures are not excluded.

So as to carry out the process of the invention starting with the above-mentioned technique, at least one of the following factors is advantageously acted on: relative proportions of the reactants, catalyst proportions, temperatures, reaction times. The presence of an excess of halo-alkane being favorable to the ratio of conversion of the salt of the acid, the reaction can be conducted with stoichiometric proportions of reactants, or even with a slight excess of the alkaline salt. The reduction of the quantity of catalyst, a slight decrease of the temperature, an appreciable diminution of the reaction time, in relation to the conditions required for a total conversion of the acid salt, make it possible, separately or in combination, to attain the objects of the present invention.

A convenient means of controlling the conversion rate of the salt of the polycarboxylic acid consists of following the evolution of the pH of the reaction mixture, and of stopping the reaction, i.e. practically to stop heating the mixture, before the pH has reached a point lower than about 4.8. It has indeed been noticed in numerous tests that the intermediate esters begin to be formed when the pH is lower than this value.

The mixture coming from the reaction contains chiefly the desired ester, the starting polycarboxylic reactant which has not reacted with the halo-alkane, the formed alkaline halide, the catalyst and optionally the excessive halo-alkane. The polycarboxylic reactant and the alkaline halide are wholly or almost wholly dissolved in the quantity of water used.

According to a further characteristic of the process of the invention, the reaction mixture is acidified with a strong mineral acid, such as hydrochloric, sulfuric acid, and so on. This acidification is accomplished after cooling the mixture to a temperature between 80°C. and room temperature for example. The non-esterified polycarboxylic reactant is thus rendered insoluble as an acid and/or acid salts thereof.

The separation of the constituents of the mixture is then very easy. The precipitate of acid and/or polycarboxylic acid salt is isolated by a simple filtration, and can be reused in the esterification reaction. An aqueous phase containing the dissolved alkaline halide is separated from the filtrate by any suitable means, such as decantation. This solution can be treated in a usual way for recovering the halogen, in particular when bromine derivatives are used.

The organic phase remaining after removal of the aqueous solution contains chiefly the desired alkyl ester; it contains optionally the excess of halo-alkane and generally a slight quantity of the corresponding alcohol. It is more often advantageous to remove the last traces of mineral halide by washing the organic phase with water; simultaneously this organic phase is neutralized by adding a water-soluble alkaline agent. It must be noted that the separation of washing water from the organic phase is more rapid and more easily accomplished than when the acid esters are present.

Should it be required, the halo-alkane and/or the alcohol is removed from the thus treated organic medium. These compounds which are lighter than the alkyl ester, are easily separated, for instance by steam distillation or distillation under a reduced pressure. The ester recovered at the bottom of the column is generally pure enough to eliminate the need for a subsequent purification-treatment. The head fraction can be recycled to the esterification reaction.

It is easily understood that the process of the invention permits obtaining very high yields of alkyl esters, in spite of the limitation of the conversion rate of the acid salt initially introduced, due to the simple and nearly quantitative recovery of the unesterified polycarboxylic reactant, which can be recycled.

The hereinafter examples, given in a non-limitative way, illustrate some methods of practical working of the process of the invention, and emphasize its advantages.

EXAMPLE 1

In this example relating to the preparation of dioctyl phthalate, the rate of conversion of the alkaline salt of the acid has been limited, by acting at the same time on the temperature and on the time of the reaction. A test utilizing the process according to the invention is given comparatively with tests directed to a high conversion of the salt. In order to show with maximal precision the eventual presence of acid ester, the reaction mass has been treated in any case with an alkaline solution, according to the prior art.

a. Tests with a high conversion ratio of the disodium phthalate.

A solution of disodium phthalate prepared by dissolving 249 g. (1.5 mole) of o-phthalic acid in 425 g. of an aqueous solution of 29% sodium hydroxide, and 695 g. (3.6 moles) of 1-bromo octane and 0.7 g. of N-dimethylamine are introduced in an autoclave fitted with an agitator.

The apparatus is purged with nitrogen, the mixture is heated to 160°C. and kept at this temperature for 2 hours under the autogenous pressure. It is cooled, and the pH of the reaction mass is measured; its value is 1.1. After the aqueous phase containing the sodium bromide has been removed, the organic phase is treated with an aqueous solution of sodium hydroxide to bring the pH to 8–9. The decantation of the phases is slow. Potentiometrically there is titrated into the alkaline solution 50 g. (0.165 mole) of octyl sodium phthalate.

After a next water washing of the organic phase the light products are distilled under vacuum, and 515 g. (1.320 mole) of dioctyl phthalate are recovered at the bottom of the column. The starting phthalic salt has practically totally reacted, giving 88% of diester and about 11% of monoester.

The previous test is reproduced, but the reaction time is reduced by one hour. The pH of the reaction mass is 3.7. A yield of 89% of diester, and 3% of monoester is obtained in relation to the phthalic salt used.

b. Tests utilizing the process according to the invention.

The previous tests are reproduced, but at a temperature of 150°C. and with a reaction time of one hour. The conversion rate is about 77%. The pH is 5.7 at the end of the reaction. The treatment of the reaction mass, which is the same as in the previous tests, show no appearance of monoester. Moreover the decantation of the organic and alkaline phases is easily accomplished. 448 g. (1.15 mole) of dioctylphthalate are recovered.

EXAMPLE 2

In this case, the rate of conversion of the salt of the acid is limited to about 80% by operating in the absence of an excess of halo-alkane, and with a relatively short reaction time.

A solution of disodium phthalate, prepared by dissolving 332 g. (2 moles) of o-phthalic acid in 565 g. of an aqueous solution of 29% sodium hydroxide with 775 g. (4 moles) of 1-bromo-alkane and 0.9 g. of N-dimethylamine is reacted. It is purged with nitrogen, then a temperature of about 160°C. is maintained for an hour. The pH of the medium is then 5.4.

The mixture is cooled at room temperature, and acidified to a pH of 3.5 with 50% sulfuric acid. A precipitate is obtained, which is separated by filtration, it contains essentially 75 g. (0.40 mole) of acid sodium phthalate, and a small quantity of sodium bromide. This acid phthalate, which corresponds with the proportion of disodium phthalate initially used, and which has not reacted, can be recycled entirely to the reaction after neutralization in basic salt.

The filtrate is decanted, to separate therefrom the aqueous solution containing the sodium bromide. The organic phase is neutralized by washing with water with an admixture of 2.2 g. of sodium bicarbonate. No presence of monooctylphthalate is detected in this washing water. The light products of the organic phase are distilled, and 612 g. (1.57 mole) of dioctyl phthalate are obtained at the bottom of the column.

EXAMPLE 3

1.5 mole of disodium phthalate in an aqueous solution, prepared as hereinabove, is reacted to a conversion rate of about 80% with 800 g. (3.2 moles) of 1-bromo dodecane, by heating the mixture at 160°C, for 1 hour and 30 minutes in the presence of 0.7 g. of N-dimethylamine. The pH of the medium is then at 5.1.

The reaction mixture is acidified and treated as in the previous example: there is obtained 607 g. (1.2 moles) of didodecyl phthalate and 50 g. (0.27 mole) of acid sodium phthalate which can be recycled to the reaction after neutralization.

The esterification is reproduced under the same conditions, but 2 g. of catalyst are employed. The pH of the medium is 1.9 at the end of the reaction. The starting phthalic salt is entirely transformed into esters, but monododecyl phthalate (0.15 mole) has also been formed, the extraction of which by alkaline washing is difficult.

EXAMPLE 4

There is introduced into an autoclave 292 g. (2 moles) of adipic acid, 650 g. of an aqueous solution of 25% NaOH, 900 g. of 1-bromo octane and 1.8 g. of N-dimethylamine. The mixture is kept at 160°C. for 2 hours, then is acidified to pH 3.5 with 45% sulfuric acid. The treatment is carried on as in the two previous examples. The unconverted adipic acid is recovered as 113 g. of a filtercake containing 92% of adipic acid (the residue is made of sodium bromide) 470 g. (1.27 mole) of dioctyl adipate are recovered.

Thus with a rate of conversion of the starting polycarboxylic reactant of 63–64%, monooctyladipate is not formed, and the reactant which has not reacted is recovered nearly entirely, and can be recycled to a subsequent operation.

EXAMPLE 5

There is introduced into 420 g. of an aqueous solution of 29% NaOH 192 g. (1 mole) of trimetallitic anhydride, 618 g. (3.2 moles) of 1-bromo octane and 1.4 g. of N-dimethylamine. It is heated at 160°C. for 2 hours. The final pH is 5.2. It is acidified to pH 1.5 and the treatment is carried on as explained hereinabove with 211 g. (0.385 mole) of trioctyl trimellitate being obtained.

EXAMPLE 6

200 g. (2 moles) of succinic anhydride, 600 g. of an aqueous solution of 27% NaOH, 900 g. of 1-bromo octane and 2.7 g. of dimethylamine are reacted. It is heated at 160°C. for 3 hours (conversion rate: 64–65%). After the medium is acidified to pH 1, it is treated as indicated previously. 414 g. of dioctyl succinate are recovered.

It will be obvious to those skilled in the art that various changes may be made without departing from the scope of the invention and the invention is not to be considered limited to what is described in the specification.

What is claimed is:

1. In a process for producing alkyl esters of polycarboxylic acids comprising the step of reacting an alkaline salt of a polycarboxylic acid, having carboxylic groups derived from saturated or unsaturated aliphatic, cycloaliphatic, aromatic, or alkylaromatic di- or polyacids with at least one halo-alkane having 6 to 20 atoms, in an heterogeneous organic-aqueous medium, in the presence of a catalyst, at a temperature between substantially 130° and 200° C during a reaction time between 30 minutes and 6 hours, the improvement wherein the production of partial esters is substantially eliminated comprising limiting the rate of conversion of the alkaline salt to between 35 to 85% so that substantially no partial esters are formed.

2. A process according to claim 1 wherein said catalyst comprises a catalytic quantity of a nitrogen compound chosen from the group consisting of ammonia, primary, secondary and tertiary amines, and salts of quaternary ammonium containing at least 10 carbon atoms.

3. A process according to claim 2 wherein the mixture coming from the reaction is acidified with a strong mineral acid.

4. A process according to claim 1 wherein the mixture coming from the reaction is acidified with a strong mineral acid.

5. A process in accordance with claim 1, wherein said reaction takes place in a closed autoclave.

6. A process in accordance with claim 1, wherein said reaction takes place under a pressure at least equal to the autogenous pressure of said reaction.

* * * * *